(12) United States Patent
Eggers et al.

(10) Patent No.: US 10,524,892 B2
(45) Date of Patent: *Jan. 7, 2020

(54) METHOD AND APPARATUS FOR DEPLOYING AND RETRIEVING OBJECTS IN A CAVITY

(71) Applicant: Adient Medical, Inc., Pearland, TX (US)

(72) Inventors: Mitchell Eggers, Pearland, TX (US); Jeremy Durack, Pearland, TX (US); Joseph Steele, Pearland, TX (US); Michael Hogan, Pearland, TX (US); Raymond Kirk, Pearland, TX (US); David Franklin, Pearland, TX (US)

(73) Assignee: ADIENT MEDICAL, INC., Pearland, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 15/586,210

(22) Filed: May 3, 2017

(65) Prior Publication Data

US 2017/0319320 A1    Nov. 9, 2017

Related U.S. Application Data

(60) Provisional application No. 62/331,291, filed on May 3, 2016.

(51) Int. Cl.
*A61M 29/00* (2006.01)
*A61F 2/01* (2006.01)
*A61F 2/95* (2013.01)

(52) U.S. Cl.
CPC .................. *A61F 2/01* (2013.01); *A61F 2/95* (2013.01); *A61F 2002/011* (2013.01);
(Continued)

(58) Field of Classification Search
CPC .... A61F 2/01; A61F 2/013; A61F 2/95; A61F 2/962; A61F 2/966; A61F 2002/011;
(Continued)

(56) References Cited

U.S. PATENT DOCUMENTS 5,192,307 A    3/1993    Wall
5,634,928 A    6/1997    Fischell et al.
(Continued)

OTHER PUBLICATIONS

International Search Report and Written Opinion issued in corresponding PCT Application No. PCT/US17/30924, dated Sep. 6, 2017. (14 pages).

(Continued)

*Primary Examiner* — Melanie R Tyson
(74) *Attorney, Agent, or Firm* — Pillsbury Winthrop Shaw Pittman LLP (57) ABSTRACT

The present invention relates generally to a method and apparatus for deploying and/or retrieving an object (e.g., a vena cava filter) in a cavity (e.g., a vena cava) using a system configured to: (i) maintain grip of the unsheathed object in the cavity until deliberately released, (ii) prevent premature release of the object in the cavity, and/or (iii) facilitate retrieval by first everting said object, then withdrawing the object through a guiding catheter (e.g., retrieval via eversion).

26 Claims, 8 Drawing Sheets

(52) U.S. Cl.
CPC . *A61F 2002/016* (2013.01); *A61F 2002/9505* (2013.01); *A61F 2002/9528* (2013.01); *A61F 2230/0006* (2013.01); *A61F 2230/0023* (2013.01); *A61F 2230/0067* (2013.01)

(58) Field of Classification Search
CPC ...... A61F 2002/9505; A61F 2002/9511; A61F 2002/9528; A61F 2002/9534; A61F 2002/954; A61F 2002/9665
See application file for complete search history.

(56) References Cited

U.S. PATENT DOCUMENTS

| | | |
|---|---|---|
| 5,681,347 A | 10/1997 | Catheart et al. |
| 5,733,330 A | 3/1998 | Cox |
| 2002/0143387 A1 | 10/2002 | Soetikno et al. |
| 2005/0049612 A1 | 3/2005 | Urbanski et al. |
| 2007/0186933 A1 | 8/2007 | Domingo et al. |
| 2013/0226222 A1 | 8/2013 | Eggers |
| 2013/0253573 A1 | 9/2013 | Agnew |
| 2014/0081314 A1* | 3/2014 | Zaver ................ A61B 17/0057 606/200 |
| 2014/0088640 A1 | 3/2014 | Devellian et al. |
| 2014/0364941 A1 | 12/2014 | Edmiston |

OTHER PUBLICATIONS

Patent Cooperation Treaty, International Preliminary Report on Patentability for PCT/US2017/030924, dated Nov. 15, 2018, pp. 1-10.

* cited by examiner

METHOD AND APPARATUS FOR DEPLOYING AND RETRIEVING OBJECTS IN A CAVITY

RELATED PATENT APPLICATIONS

This application claims priority to U.S. Provisional Application Ser. No. 62/331,291, filed May 3, 2016, which application is incorporated herein by reference in its entirety.

FIELD OF THE INVENTION

The present invention relates generally to a method and apparatus for delivering and retrieving an object (e.g., a vena cava filter) in a cavity.

BACKGROUND OF THE INVENTION

Between 100,000 to 300,000 Americans die annually from pulmonary embolism (PE), which is more than breast cancer, AIDS, and traffic fatalities combined. PE is the 3rd leading cause of death in the United States. A similar incidence of PE is found in Europe with approximately 370,000 annual deaths. Moreover, PE is the third most common cause of death in trauma patients that survive the first 24 hours. An estimated 25% of all hospitalized patients have some form of deep vein thrombosis (DVT), which is often clinically unapparent unless PE develops. On average, 33% of DVT will progress to symptomatic PE, of which 10% will be fatal.

Risk factors for PE arising from DVT follow Virchow's Triad: (i) endothelial injury, (ii) hypercoaguability, and (iii) hemodynamic changes (stasis or turbulence). Specific at risk situations include hip and knee arthroplasty, abdominal, pelvic and extremity surgeries, pelvic and long bone fractures, major spine and brain trauma, prolonged immobility such as prolonged hospital stays and air travel, paralysis, advanced age, prior DVT, cancer, obesity, chronic obstructive pulmonary disease, diabetes, congestive heart failure, and other situations. Patients undergoing orthopedic procedures can carry a higher (e.g., 40-80%) risk for DVT and PE following knee and hip surgeries in the absence of prophylactic treatment, for example.

The American Academy of Orthopedic Surgeons (AAOS) has issued guidelines for PE prophylaxis. According to the AAOS, patients at standard risk of PE prophylaxis should be considered for chemoprophylactic agents such as aspirin, low molecular weight heparin (LMWH), synthetic pentassaccharides, or warfarin, in addition to intra-operative and/or immediate postoperative mechanical prophylaxis.

The duration of prophylaxis depends on the source of potential DVT. Current recommendations for prophylaxis comprise a minimum of seven to ten days for moderate to high risk surgeries and up to 28-35 days for many orthopedic surgeries. Studies indicate that hypercoaguability persists for at least one month after injury in about 80% of trauma patients. Overall, prophylactic treatment for possible venous thromboembolism (VTE), which is DVT and PE combined, is often warranted for up to 35 days following trauma or major surgery.

Contraindications for chemoprophylaxis include active bleeding, hemorrhagic diathesis, hemorrhagic stroke, neurologic surgery, extensive trauma, hemothorax, pelvic or lower extremity fractures with intracranial bleeding, and anticoagulation interruption.

For patients who are contraindicated for the above-mentioned anti-coagulation prophylaxis, or where anti-coagulation therapy has failed, the Society of Interventional Radiology, AAOS, American College of Physicians, and the British Committee of Standards in Haematology recommend the use of venous filters. These intravascular blood filters are typically deployed via catheter into the inferior vena cava (IVC) to catch emboli arising from lower extremity DVT before reaching the heart or pulmonary arterial circulation. Furthermore, the British Committee of Standards in Hematology recommends IVC filter placement in pregnant patients who have contraindications to anticoagulation and develop extensive VTE shortly before delivery (e.g., within 2 weeks).

The Eastern Association for Surgery of Trauma further recommends prophylactic IVC filters placed in trauma patients who are at increased risk of bleeding and prolonged immobilization. Such prophylactic recommendation follows studies that demonstrate a low rate of PE in patients with severe polytrauma who underwent IVC filter placement. A systematic study on the effectiveness of prophylactic IVC filters in trauma patients revealed a consistent reduction in PE with a relative risk of 0.20. Hence, in controlled clinical studies, trauma patients are about five times more likely to have a PE without an IVC filter. Moreover, analysis has revealed that no fatal PEs occurred in the IVC filter arms of any of the included studies, yet 20 fatal PEs occurred in the 407 patients not receiving IVC filters.

Many IVC filters installed were expected to be permanent fixtures since endothelialization usually occurs within 7-10 days, making some models impractical to remove without irreversible vascular damage, potentially leading to life threatening bleeding, dissection of the IVC, and/or thrombosis. Although these permanent filters have prevented PE, they have been shown to actually increase the risk of recurrent DVT over time. For example, in one randomized controlled trial the incidence of DVT within the IVC filter cohort increased almost two times: (i) a 21% incidence of recurrent DVT in the filter cohort vs. 12% in the non-filter cohort at 2 years ($p=0.02$), and (ii) a 36% incidence of recurrent DVT in the filter cohort versus 15% in the non-filter group at 8 years ($p=0.042$). The filters did reduce the occurrence of PE. The filter cohort experienced only 1% PE versus the non-filter cohort posting 5% PE in the first 12 days ($p=0.03$). Apparently the initial benefit of reduced PE with permanent IVC filters is offset by an increase in DVT.

In addition to increased incidence of DVT for prolonged IVC filter deployment, filter occlusion has been reported with some models at about a 6% to 30% occurrence, as well as filter migration (about a 3% to 69% occurrence), venous insufficiency (about a 5% to 59% occurrence), and post thrombotic syndrome (about a 13% to 41% occurrence). Complications from insertion including hematoma, infection, pneumothorax, stroke, air embolism, misplacement, device migration, vein perforation, arteriovenous fistula, and inadvertent carotid artery puncture have an occurrence rate of about 4%-11%.

Retrievable IVC filters have been marketed more recently. Retrievable IVC filters are intended to be removed when the indication has expired, and hence circumvent many of the deleterious complications of permanent filters such as increased risk of DVT. The retrievable filters feature flexible hooks, collapsing components, fewer barbed struts, unrestrained legs, and/or other features to ease retrieval. Unfortunately, many of these same features have led to unwanted side effects, including filter migration, fatigue failure leading to fracture, IVC penetration, fragment migration to hepatic veins and pulmonary arteries, filter tilt, and metallic emboli, for example. In a recent study perforation of the IVC by leading retrievable IVC filters was shown to be the rule, not the exception, as about 86% of the filters on computed tomography (CT) scans obtained between 1 and 880 days after filter placement had perforated the IVC. These adverse events prompted the Food and Drug Administration (FDA) to issue a formal communication stating that "FDA recommends that implanting physicians and clinicians responsible for the ongoing care of patients with retrievable IVC filters consider removing the filter as soon as protection from PE is no longer needed." Moreover, in 2014, a second communication released by the FDA recommended that retrievable IVC filters be removed between 29 and 54 days after deployment for patients in whom the transient risk of PE has passed. Even though these types of retrievable filters are often intended to be removed within approximately 3 months, at which time the technical retrieval success rate is 94% (versus 37% at 12 months), several studies indicate that approximately 70%-80% of patients with retrievable filters do not return to the hospital for subsequent filter retrieval.

Due to the mounting complications of metallic retrievable IVC filters following extended indwelling times, combined with the reluctance of patients to return for IVC filter retrieval, fully absorbable IVC filters have been proposed that obviate retrieval by simply breaking down into carbon dioxide and water and/or other materials several months following the risk period for PE. Furthermore, these absorbable IVC filters are much more flexible than conventional metal IVC filters rendering them less capable of perforating the IVC and impaling neighboring organs.

SUMMARY OF THE INVENTION

The present invention relates generally to a method and apparatus for deploying and retrieving an object (e.g., a vena cava filter) in a cavity using a catheter configured to: (i) maintain grip of the unsheathed object in the cavity until deliberately released, (ii) prevent, using an interlock and/or other devices, premature release of the object in the cavity, and/or (iii) facilitate retrieval by first everting said object, then withdrawing the object through a guiding catheter (e.g., retrieval via eversion). In some embodiments, the present invention relates to a method and apparatus for the deployment and retrieval of a flexible vena cava filter. An example of such a filter is described in U.S. patent application Ser. No. 13/403,790 entitled "Absorbable Vascular Filter" filed Feb. 23, 2012, which is hereby incorporated by reference in its entirety.

Most conventional IVC filters, when released from a catheter, spring outward and are secured with metallic barbs at the release site in the IVC, with no opportunity for repositioning. Moreover, these prior art devices generally cannot be retrieved without a separate retrieval system that often requires jugular access. In typical retrieval methods, a catheter-based extraction device secures the tip of the filter for cephalad retrieval through a guiding catheter inserted in the jugular vein.

In contrast, the present invention enables the user to maintain grip of an IVC filter, enabling repositioning of the filter in the IVC following unsheathing of the filter, as well as offering the option to retrieve the filter by everting and pulling the filter in a proximal direction into the same catheter system used during deployment (e.g., retrieval via eversion). This retrieval technique is convenient, for example, if an IVC filter deployed through the femoral vein has to be retrieved immediately following deployment due to malposition and/or for other reasons, since the same guiding catheter used to deploy the filter can be used to retrieve the filter, thereby eliminating the need for jugular access and/or additional components and/or equipment.

The disclosed IVC filter deployment and retrieval via eversion method and apparatus is suitable for filters fabricated from flexible materials such as absorbable filaments, polymers, metal alloys, and/or other materials. In the event an absorbable filter, for example, must be retrieved before it has been absorbed in the IVC, the present invention enables efficient retrieval from a position caudal to the filter and/or other positions. For example, if an absorbable filter is catheter deployed from the femoral vein into the IVC, it can be easily retrieved using the present system by grasping and pulling the filter tip proximally, or caudally causing the flexible filter to evert in the IVC, much like pulling a sock inside out, and pulling the filter into the guiding catheter. Once secure in the guiding catheter, the assembly including the guiding catheter and errantly placed (for example) IVC filter may be removed from the patient through the femoral vein, for example.

In some embodiments, the eversion method may be used with the present system to retrieve various objects from the vascular system including IVC filters, guidewires, stents, coils, portions of medical devices such as cardiac leads and other fractured implants, and/or other objects.

BRIEF DESCRIPTION OF THE DRAWINGS

FIG. 7 is a view of the delivery system with a flexible IVC filter compressed and preloaded over a balloon at the distal end. FIG. 7 also reveals a syringe with pressure gauge coupled to the delivery system for optional ballooning of the IVC filter, together with ancillary components including the guiding catheter and/or introducer and dilator.

DETAILED DESCRIPTION OF THE INVENTION

Embodiments of the present invention will now be described in detail with reference to the drawings, which are provided as illustrative examples so as to enable those skilled in the art to practice the invention. Notably, the figures and example below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting. Rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration. The terms "proximal" and "distal" are used with reference to the operator of the extraction device. In particular the distal end will be nearest to the object of extraction, while the proximal end will be nearest to the operator.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The present invention relates generally to a method and apparatus for deploying and retrieving an object (e.g., a vena cava filter) in a cavity using a catheter configured to: (i) maintain grip of the unsheathed object in the cavity until deliberately released, (ii) prevent, using an interlock, premature release of the object in the cavity, and/or (iii) facilitate retrieval by first everting said object, then withdrawing the object through a guiding catheter (e.g., retrieval via eversion).

Although the present invention can be used to deploy and retrieve a plethora of implantable medical devices in a cavity, deployment and retrieval of a flexible IVC filter intended to prevent pulmonary embolism (PE) is shown and described herein as one example embodiment to illustrate details of the present method and apparatus. The flexibility of such an IVC filter often requires ballooning during deployment, which poses both new challenges and opportunities for their accompanying delivery systems. For example, the increased flexibility of absorbable IVC filters enables retrieval via the eversion method described herein (e.g., in the event that the filter must be retrieved before resorption). Consequently there is a current demand for the novel delivery system described herein that can both accommodate and exploit the unique features of a flexible IVC filter and/or other filters.

First, the retrieval via eversion method and apparatus will be described using miniaturized grasping forceps to extract a flexible IVC filter subsequent to deployment. Following such description, the delivery system method and apparatus allowing both deployment and retrieval of a flexible IVC filter will be described in detail with the featured interlock mechanism to prevent premature filter release. It should be noted, that even though these descriptions are treated somewhat separately, both of these descriptions refer to the components and operation of present system 100.

Referring to FIGS. 1-5, a vessel and/or cavity 5 such as the inferior vena cava (IVC) and/or other vessels and/or cavities is shown to house (i) an IVC filter 4 comprising an inferior "stent" portion 50 comprised of a high density weave of flexible filament (for example) to maintain filter positioning within IVC 5 (e.g., by pressing against a wall of the IVC) and a superior "capture basket" 51 comprising a low density weave of flexible filament (for example) to capture thrombus, (ii) a guiding catheter 1 (e.g., a portion of system 100) placed in vena cava 5 typically by insertion into the femoral vein (but this is not intended to be limiting) that serves as a conduit to the location 52 within IVC 5 for filter 4 placement, and (iii) extraction device catheter 2 (e.g., another portion of system 100) housing the extraction or grasping components and/or device 53 at the distal end 3 of catheter 2 and the actuator controls (not shown in FIGS. 1-5) at the proximal end 54.

Figure 1:
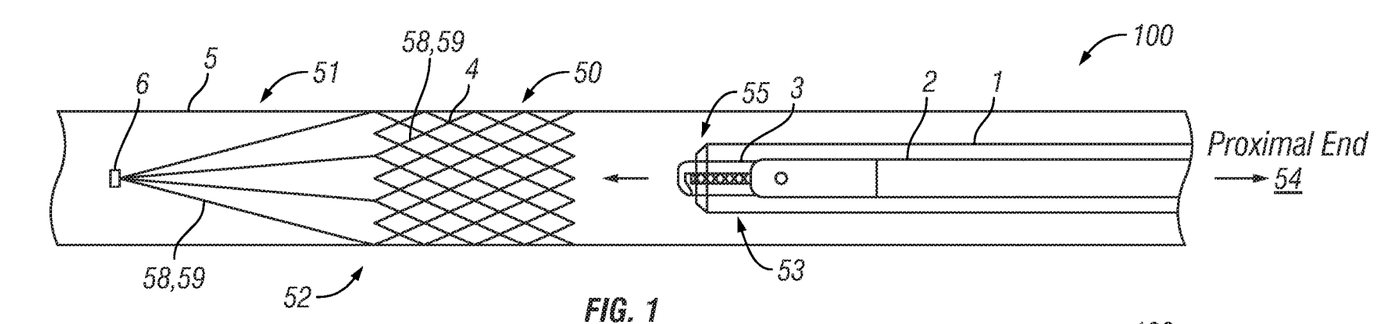
FIG. 1 is a cut-away isometric view of the first of a series of figures (FIGS. 1-5) detailing a method of retrieving (e.g., via eversion) a flexible IVC filter using a catheter-based extraction device from a position inferior to the filter, or equivalently, proximal to the operator. Here the extraction device is positioned at the distal end of the guiding catheter.
Figure 2:
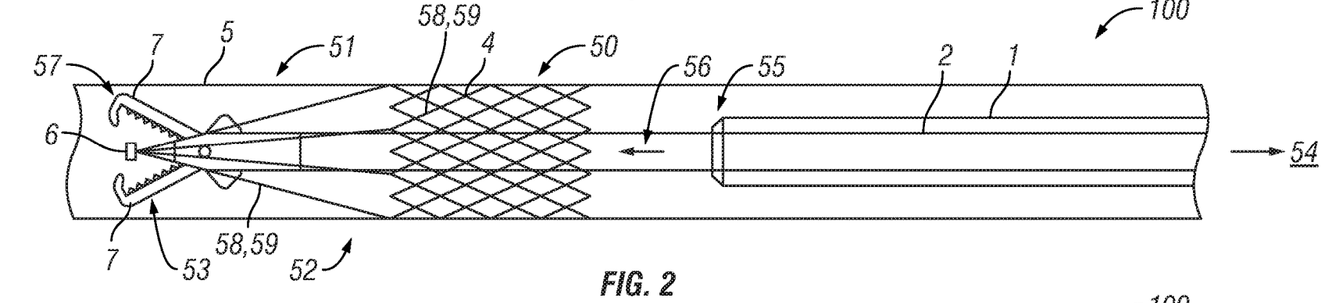
FIG. 2 is a cut-away isometric view of the second of a series of figures (FIGS. 1-5) detailing the method of retrieving (e.g., via eversion) a flexible IVC filter using a catheter-based extraction device from a position inferior to the filter, or proximal to the operator. Here the extraction device is opened and in position to grasp the tip of the filter.

FIG. 1 depicts the distal end 3 of the extraction device 53 in the closed position (e.g., fully collapsed jaws) advanced to a position at the distal end 55 of the guiding catheter 1. The extraction device catheter 2 is further advanced 56 into the IVC filter 4 (e.g., through an interior of portions 50 and 51) to reach the (e.g., distal) end or tip 6 of the IVC filter 4 as shown in FIG. 2. Once the distal end 57 of the extraction device 53 is within proximity of the (e.g., distal) tip 6 of the IVC filter 4, the controls (not shown in FIG. 2) are actuated by the operator at the proximal end 54 of the extraction device catheter 2 to open the jaws 7 of the extraction device 53 to grasp the tip 6 of the IVC filter 4. Alternatively, the distal end 57 of the extraction device 53 could grasp a leg 58 or strut 59, or the other end of the filter 4.

Figure 3:
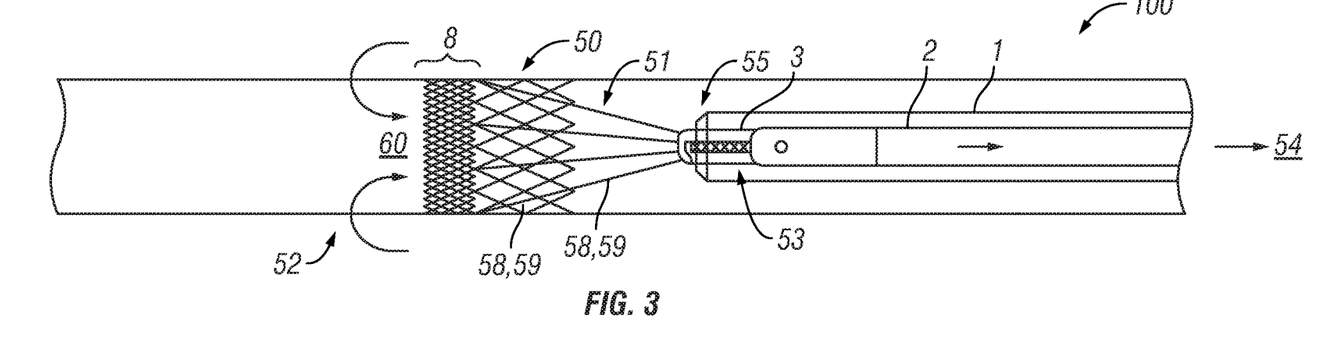
FIG. 3 is a cut-away isometric view of the third of a series of figures (FIGS. 1-5) detailing the method of retrieving (e.g., via eversion) a flexible IVC filter using a catheter-based extraction device from a position inferior to the filter, and/or proximal to the operator. Here the extraction device has secured the tip of the filter and the operator has pulled the filter proximal into the guiding catheter causing the flexible IVC to commence eversion.
Figure 4:
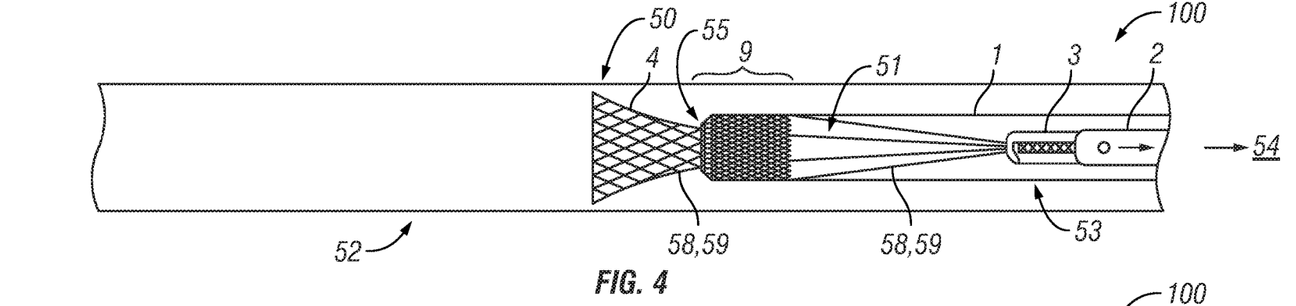
FIG. 4 is a cut-away isometric view of the fourth of a series of figures (FIGS. 1-5) detailing the method of retrieving (e.g., via eversion) a flexible IVC filter using a catheter-based extraction device from a position inferior to the filter, or proximal to the operator. Here the extraction device is within the guiding catheter as the operator has everted the filter.

Following secure grasping of the IVC filter 4 tip 6, the extraction device catheter 2 is gently pulled proximally towards the operator (e.g., toward end 54) causing the IVC filter 4 to evert 60 as shown in FIG. 3. During eversion 60, regions of the stent portion 50 of the IVC filter 4 will be pulled inside the outer circumferential regions of the stent portion 50 of the IVC filter 4 as depicted in region 8 (e.g., after portion 51 has also passed through). Continued pulling of the extraction device catheter 2 by the operator will facilitate complete eversion 60 of the IVC filter 4 with the filter capture basket 51 now being inferior with respect to the stent portion 50 of the filter 4 as shown in FIG. 4, which is about 180° opposite from the original position 52 of the filter 4 (e.g., inverted via eversion). That is, the IVC filter 4 is now positioned with the tip 6 and/or capture basket 51 proximal, and the stent portion 50 distal. Also as depicted in FIG. 4, the stent portion 50 of the flexible IVC filter is compressed in region 9 as it enters the guiding catheter 1.

Figure 5:
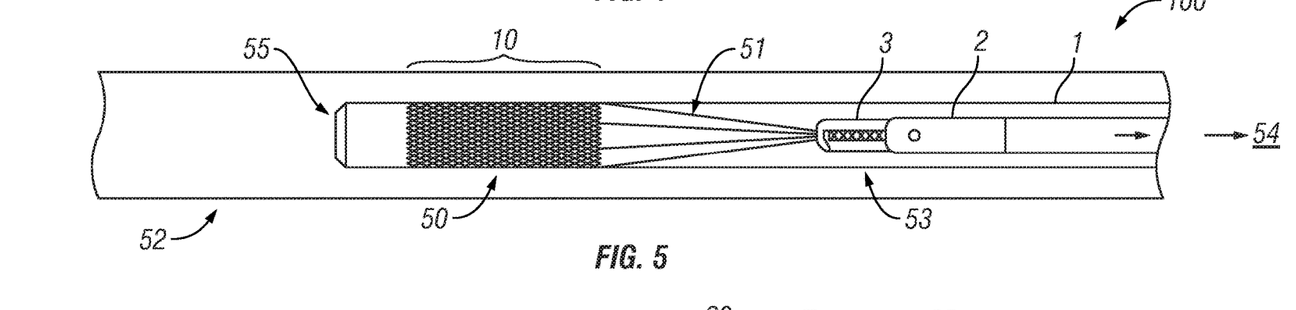
FIG. 5 is a cut-away isometric view of the fifth of a series of figures (FIGS. 1-5) detailing the method of retrieving (via eversion) a flexible IVC filter using a catheter-based extraction device from a position inferior to the filter, or proximal to the operator. Here the extraction device is positioned well within the guiding catheter such that the everted IVC filter is secure within the guiding catheter and ready to be removed from the body as an integrated unit.

FIG. 5 depicts the IVC filter 4 completely everted and secured within the guiding catheter 1. Region 10 shows the stent portion 50 of the IVC filter 4 compressed within the guiding catheter 1. The operator can now remove the entire assembly including the guiding catheter 1 and extraction device catheter 2 with the captured and/or attached IVC filter 4 from the body (e.g., vena cava 5).

Figure 6:
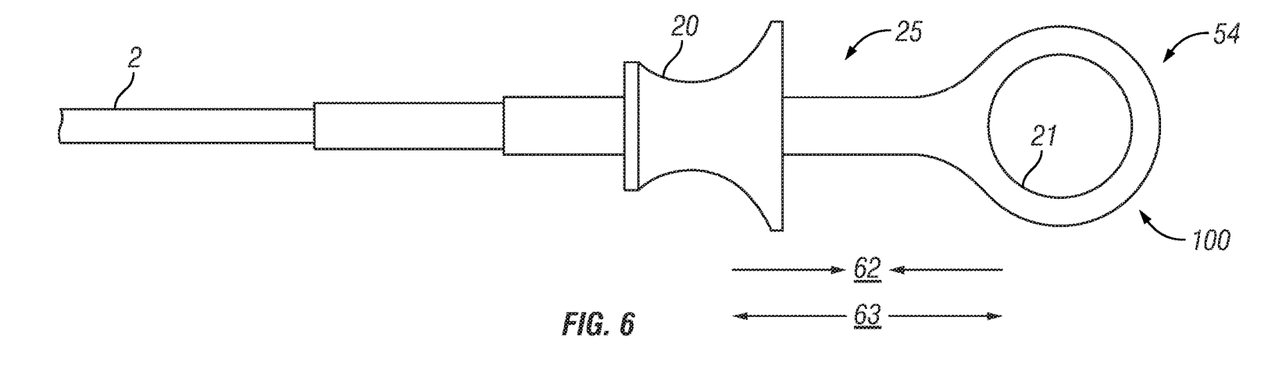
FIG. 6 is a view of the proximal end of the extraction device featuring a handle used to actuate the distal end of the extraction catheter to effect the grasping of the IVC filter.

FIG. 6 illustrates the proximal end 25 of the extraction device catheter 2 comprising a sliding handle 20, a thumb grip 21, and/or other components. In one embodiment, the sliding handle 20 and thumb grip 21 are compressed 62 relative to each other to close the jaws 7 (FIG. 2) at the distal end 57 of the extraction device catheter 2, while extending 63 the sliding handle 20 and thumb grip 21 relative to each other will open the jaws 7. The actuation for opening and closing the grasping mechanism (e.g., extraction device 53) can be built from cables or flexible rods, and/or other methods as known in the art.

FIGS. 7-18 illustrate deploying and retrieving a flexible IVC filter. For example, FIG. 7-18 illustrate: (i) maintaining a grip on an unsheathed filter in the IVC until deliberately released, (ii) interlocking preventing premature release of the filter in the IVC, and (iii) retrieval by first everting said filter and then withdrawing it through a guiding catheter (e.g., retrieval via eversion).

Figure 7:
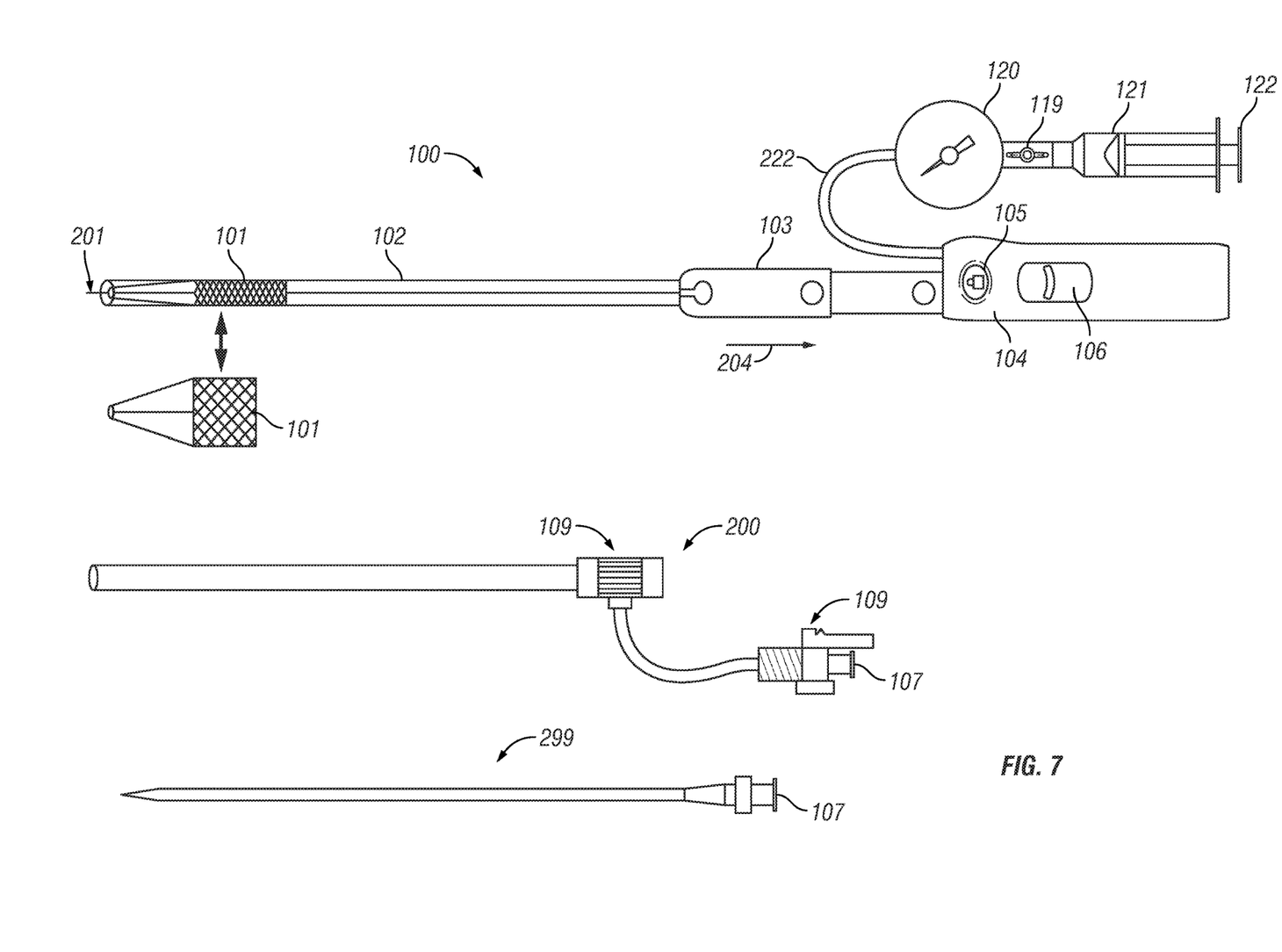

FIG. 7 illustrates delivery system 100 and ancillary components including a guiding catheter and/or introducer 200 (e.g., similar to and/or the same as guiding catheter 1 described above), a dilator 299 that is inserted in the introducer 200 over a guide wire 201 for IVC filter deployment, a valve 119, a pressure gage 120 that indicates pressure of liquid in delivery system 100 (e.g., contrast solution and/or other liquids forced into delivery system 100 by plunger 122), tubing 222 that conducts fluid from the pressure gage 120 and plunger 122 to other components of the present system (e.g., as described herein), various luer fittings 107 and/or other coupling components 109 configured to removably couple one or more components of the present system to each other and/or outside systems, and/or other components. The delivery system 100 includes a handle 104, safety release indicator 105 (e.g., shown in locked position), filter release switch 106, unsheathing barrel slide 103, outer catheter 102, preloaded flexible IVC filter 101 (e.g., which is similar to and/or the same as filter 4 described above), and/or other components.

Figure 8:
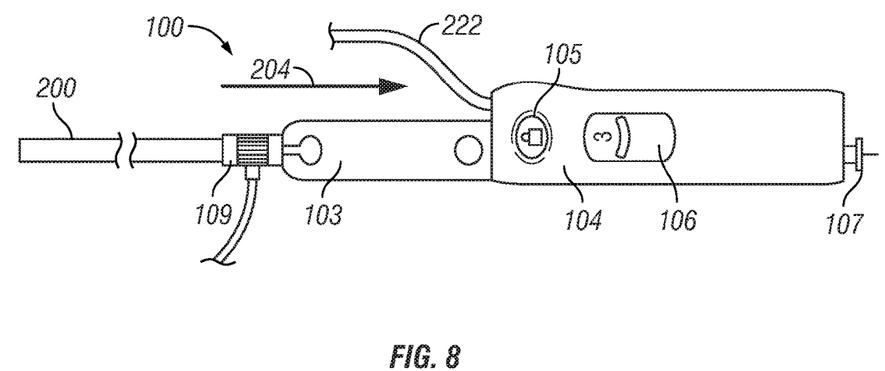
FIG. 8 is a view of the delivery system during the first step of IVC filter deployment, namely unsheathing the filter.

Filter deployment with the delivery system 100 includes pulling (e.g., by an operator) the barrel slide 103 proximally 204, which effectively pulls the outer catheter 102 and introducer 200 proximally 204 to unsheathe the filter 101 as shown in FIGS. 7 and 8. It should be noted that the introducer 200 is coupled with the barrel slide 103 such that when the barrel slide 103 is pulled proximally 204, both the introducer 200 and outer sheath 102 are no longer positioned over the compressed IVC filter 101.

Figure 9:
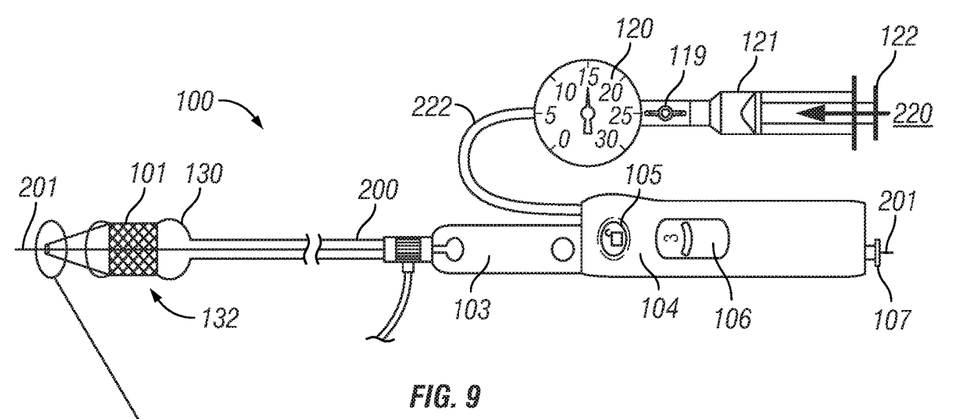
FIG. 9 is a view of the delivery system during the second step of IVC filter deployment, namely ballooning the filter to achieve caval apposition.

Filter deployment with the delivery system 100 includes "ballooning" the compressed flexible IVC filter 101 (e.g., expanding the diameter of the IVC filter 101 compressed over the balloon to fit snug against the IVC wall) as shown in FIG. 9. As shown in FIG. 9, a plunger 122 of a syringe 121 filled with diluted contrast solution and/or other materials is pushed (e.g., by an operator) distally 220, forcing contrast solution into the balloon 130 (e.g., through tubing 220 and/or tubing included in catheter 200), thereby expanding the diameter of the filter 101 in the IVC to ensure caval apposition, for example. As caval apposition is achieved (and/or at other times), the semi-compliant (for example) balloon 130 may form a "dog bone" shape 132 that may be revealed on a fluoroscope and/or other equipment (for example).

Figure 10:
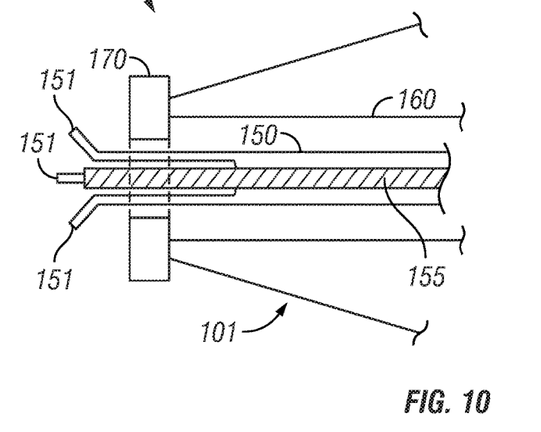
FIG. 10 is a magnified view of the distal end of the delivery system prior to IVC filter release showing a mechanism that retrains the filter at the distal tip until it is deliberately released.

As shown in the magnified view in FIG. 10, the filter 101 is retained during the ballooning step by the retention tube 150 with retention fingers 151 that prevent the distal tip 170 of the IVC filter 101 from migrating downstream. Once the balloon 130 (FIG. 9) forms the "dog bone" shape (for example) indicating caval apposition, it can be subsequently evacuated by pulling the plunger 122 (FIG. 9) proximally.

Figure 11:
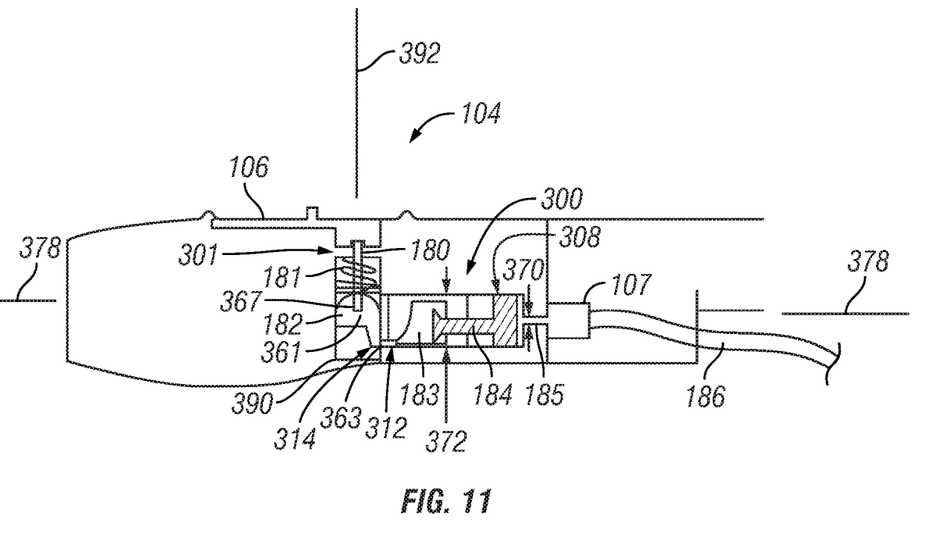
FIG. 11 is a view of the internal mechanical workings of the delivery system within the handle revealing an interlock feature that prevents the filter from being deployed before caval apposition has been achieved. The shown state is "locked" whereby a pin in the filter release slide switch prevents the user from releasing the filter.
Figure 12:
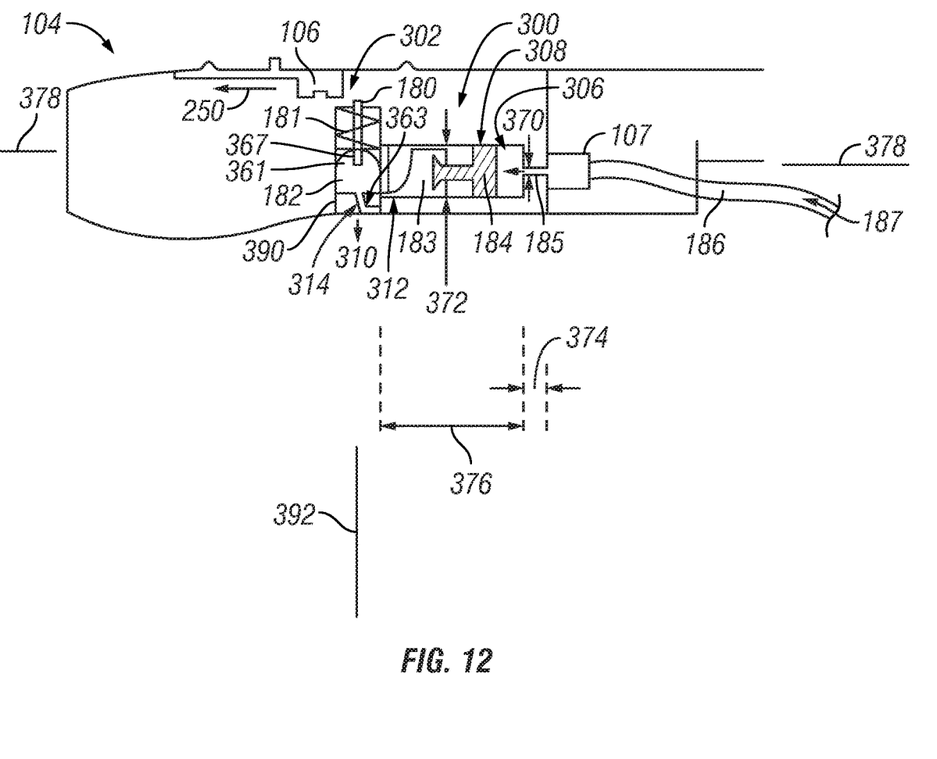
FIG. 12 is a view of the internal mechanical workings of the delivery system within the handle revealing the interlock feature that prevents the filter from being deployed before caval apposition has been achieved. The shown state is "unlocked" whereby the pin is no longer preventing the proximal sliding of the switch to release the filter.

An interlock mechanism 300 within the handle 104 (FIG. 9) of the delivery system 100 (FIG. 9) is shown in FIGS. 11 and 12. The interlock mechanism 300 is configured to facilitate prevention of premature release of the IVC filter 101 (FIG. 9), that is, releasing the filter 101 before caval apposition is achieved. FIG. 11 illustrates the interlock mechanism in the "locked" state 301 whereby the release switch 106 is prevented from sliding proximally 250 (FIG. 12) by the pin 180 that is recessed into the release switch 106. The release switch 106 is coupled with the interlock rod 155 (described below) and the retention tube 150 (described below) that together retain the filter 101 with the delivery system 100, thereby preventing premature release of the filter (e.g., as described below).

FIG. 12 illustrates the interlock mechanism 300 in the "unlocked" state 302 that occurs once the balloon 130 (FIG. 9) has reached a designated pressure (for example) corresponding to caval apposition, typically about 15 psi and/or other pressures for IVC filter applications, for example. During the ballooning process, the increased balloon pressure 187 within the tube 186 (which is similar to and/or the same as tubing 222 described above) leading to the interlock mechanism 300 will force 306 the piston 184 to slide within a cylinder 308 which in turn causes the spring loaded trigger 182 to fall 310 since a portion 314 of trigger 182 is positioned on a ledge 312 in contact with the piston 184 indirectly through the translator 183. As the spring loaded trigger 182 (note spring 181) falls 310 (and/or is pushed by spring 181), the pin 180 disengages from the release switch 106 allowing the IVC filter to be released. The translator 183 is configured to deliver force from the piston 184 to the bottom (for example) of the trigger 182 that is positioned on the ledge 312.

In some embodiments, the spring loaded trigger 182 includes a body 361, a foot portion 363, a leg portion 365 extending between the body 361 and the foot portion 363, and/or other components. In some embodiments, body 361 includes a sleeve, groove, and/or other components 367 configured to receive an end of the pin 180. The foot portion 363 is operatively coupled to the piston 184 via translator 183. The foot portion 363 is supported by the ledge 312 and configured to be pushed off the ledge 312 by the piston 184 (via translator 183) and cause the spring loaded trigger 182 to disengage the release switch 106 (e.g., when body 361, leg portion 365, and foot portion 363 fall 310 (and/or are pushed by spring 181). In some embodiments, the ledge 312 is formed by a portion of cylinder 308. In some embodiments ledge 312 is formed by a portion of cylinder 308 that is opposite orifice 185 (described below). In some embodiments, leg portion 365 extends from body 361 toward ledge 312 such that foot portion 363 rests on ledge 312 as shown and described.

Orifice 185 is configured to facilitate avoidance of erroneous triggering of the interlock mechanism 300 in the event the operator pushes the syringe plunger 122 (FIG. 9) abruptly, causing a temporary spike in balloon pressure, well before caval apposition is achieved at the steady state pressure of approximately 15 psi (for example). The diameter 370 of orifice 185 is sized to prevent such pressure spikes that could inadvertently trigger the interlock mechanism 300. In some embodiments, the orifice 185 has a cylindrical cross section with a diameter 370 that is smaller than a diameter 372 of the cylinder 308 and a length 374 that is shorter than a length 376 of the cylinder 308. In some embodiments, diameter 370 is up to about 5 mm. In some embodiments, diameter 370 is between about 0.25 mm and about 1 mm. In some embodiments, diameter 370 is about 0.5 mm. In some embodiments, diameter 372 is up to about 20 mm. In some embodiments, diameter 372 is between about 5 mm and about 20 mm. In some embodiments, diameter 372 is about 10 mm.

In some embodiments, orifice 185 and cylinder 308 are oriented along a first axis 378 of handle 104 such that length 374 and length 376 extend along axis 378. In some embodiments, spring loaded trigger 182, spring 181, and pin 180 occupy a second cylinder 390 that is oriented along a second axis 392 of handle 104. In some embodiments, second axis 392 and first axis 378 are substantially perpendicular to each other. In some embodiments, spring loaded trigger 182 falls 310 (and/or is pushed by spring 181) in cylinder 390 responsive to foot portion 314 of trigger 182 sliding off of ledge 312 when pushed by the translator 183 and the piston 184.

Figure 13:
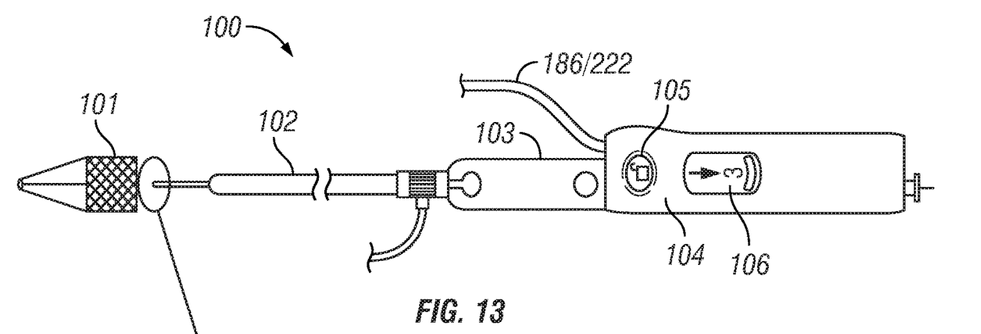
FIG. 13 is a view of the delivery system during the third step of the IVC filter deployment, namely releasing the filter.
Figure 14:
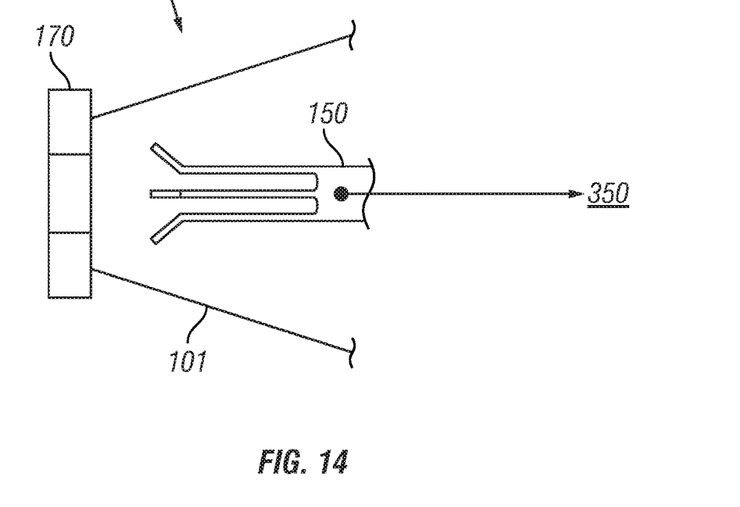
FIG. 14 is a magnified view of the distal end of the delivery system following release of the IVC filter revealing the retention mechanism in the released state.
Figure 15:
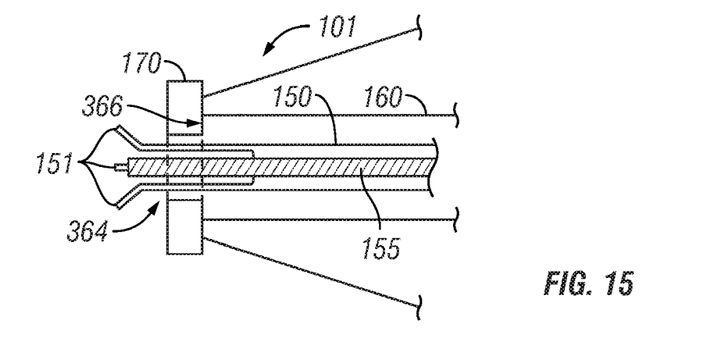
FIGS. 15-18 reveal the step by step process of releasing the filter showing the retention mechanism in several sequential positions.
Figure 16:
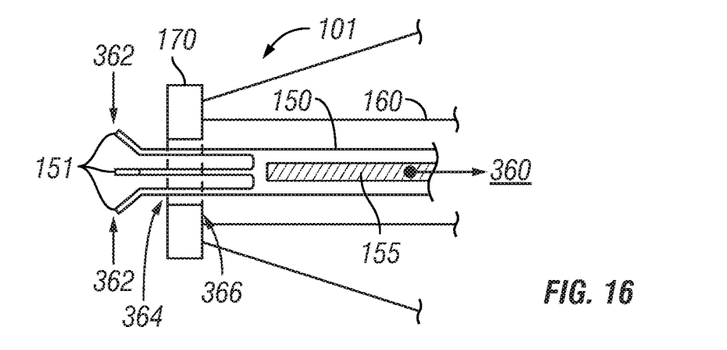
Figure 17:
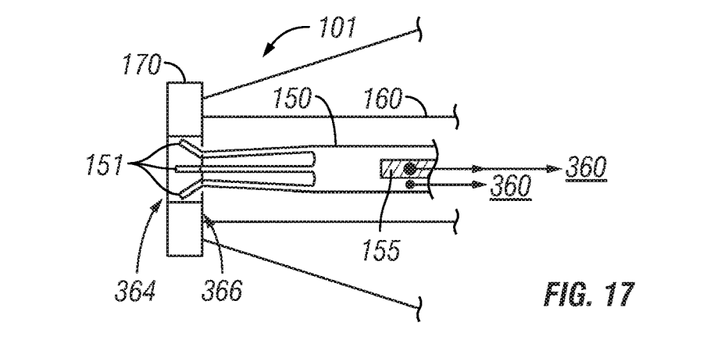

Delivery system 100 (FIG. 9) facilitates releasing the filter 101 (FIG. 9) by sliding the release switch 106 proximally 250 (FIG. 12) once the interlock mechanism 300 is disengaged (FIG. 12). In some embodiments, delivery system 100 is configured such that disengagement (and/or conversely engagement) of interlock mechanism 300 is indicated by an indicator on handle 104 and/or other components of delivery system 100. For example, FIG. 13 illustrates an unlocked padlock symbol 105 (which would show as locked if mechanism 300 was engaged). The indicator can be changed from a locked symbol to an unlocked symbol (both symbols printed on a lever) by a spring-loaded sliding lever that is substantially simultaneously activated by triggering of the interlock mechanism 300. A magnified view of the retention tube 150 and the retention fingers 151 with handle 104 in the "unlocked" state is shown in FIG. 14. Here the retention tube 150 has been pulled proximally 350 relative to the distal tip 170 of the IVC filter 101, thereby no longer being in contact with the filter 101.

Figure 18:
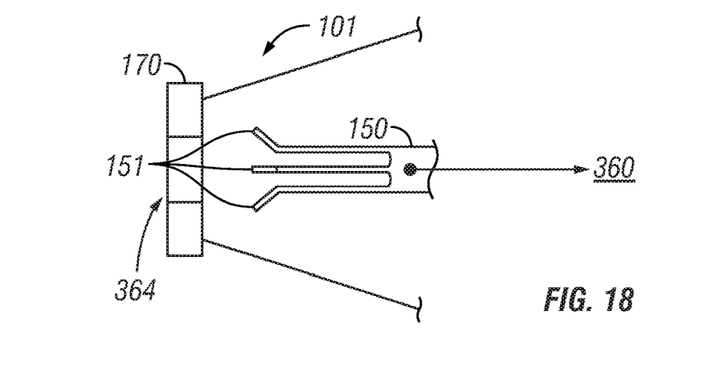

A series of magnified figures (FIGS. 15-18) illustrate the sequential release of the IVC filter 101 from the delivery system 100 (FIG. 7-9) by sliding and/or otherwise moving the filter release switch 106 (FIG. 9) proximally 250 (FIG. 12). As the filter release switch 106 is moved proximally 250, a first inner lock rod 155 slides and/or otherwise moves proximally 360, enabling and/or otherwise facilitating the collapse 362 (e.g., pinching toward each other) of the retention fingers 151. The retention fingers 151 on the retention tube 150 collapse as they traverse proximally through the center hole 364 of the IVC filter 101 distal tip 170 as detailed in FIGS. 16 and 17, for example. In some embodiments, another tube such as the balloon tube 160 provides a backstop 366 preventing proximal motion of the IVC filter 101 while the retention tube 150 and lock rod 155 are pulled proximally 360. Once the retention fingers 151 are positioned proximal to the distal tip 170 of the IVC filter 101, the filter 101 is easily released as shown in FIG. 18. In some embodiments, retention tube 150 and/or lock rod 155 may be and/or include stainless steel (and/or other materials) hypotubes (and/or other devices), for example.

In some embodiments, e.g., when it is desired to retrieve the IVC filter immediately following insertion in the IVC due to malposition, inappropriate sizing, and/or for other reasons, it is possible to use the retention mechanism represented, for example, by the retention fingers 151 of the retention tube 150 together with the lock rod 155 in the lock position (e.g., FIG. 10, 15) to facilitate retrieval via eversion and/or other methods, for example. In such embodiments, the introducer 200 may be uncoupled from the delivery system barrel 103 (FIG. 13) and the delivery system handle 104 may be pulled proximally, while the introducer 200 is held substantially stationary. Since the retention fingers will remain distal to the filter end plate 170 in the locked position, this effort will cause the flexible IVC filter 101 (e.g., attached to the delivery system 100 by the retention mechanism) to evert and be pulled into the introducer 200 for easy removal without requiring any additional components or equipment.

It should be noted that the shapes (e.g., cylindrical, etc.) and dimensions described herein are not intended to be limiting. The components of the present system may have any shape and/or size that allows them to function as described herein.

Figure 19:
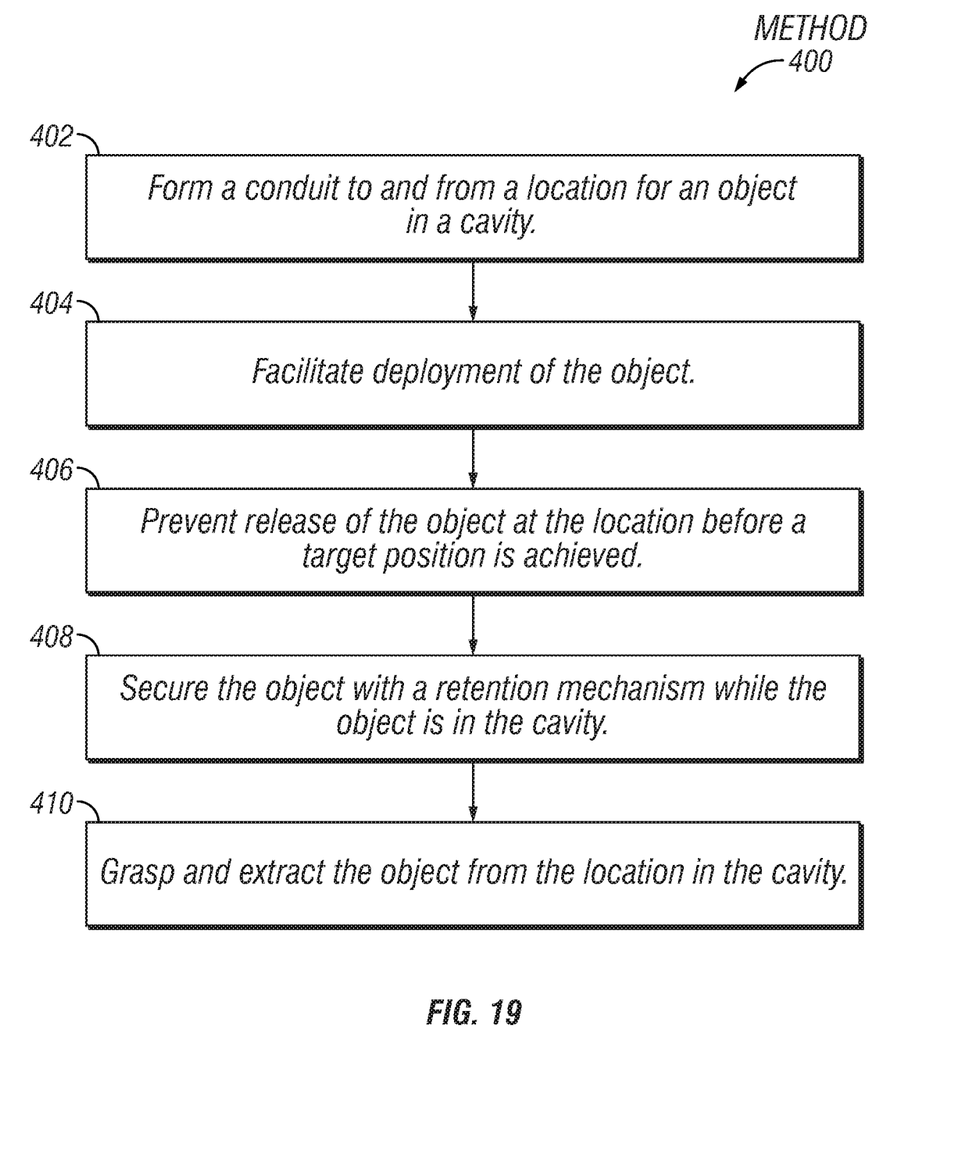
FIG. 19 illustrates a method for delivering an object to, and retrieving an object from, a location in a body cavity with a delivery system.

FIG. 19 illustrates a method 400 for delivering an object to, and retrieving an object from, a location in a body cavity with a delivery system. The system comprises a guiding catheter, object deployment components, an interlock mechanism, a retention mechanism, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 19 and described below is not intended to be limiting.

At an operation 402, a conduit is formed to and from the location for the object in the body cavity. In some embodiments, operation 402 is performed by a guiding catheter similar to and/or the same as guiding catheter 1 (shown in FIG. 1 and described herein) and/or guiding catheter 200 (shown in FIG. 7 and described herein).

At an operation 404, deployment of the object is facilitated. In some embodiments, deployment is facilitated with object deployment components. In some embodiments, the object deployment components comprise a balloon configured to expand the object at the location, a pressure gage, fluid, a plunger, and/or other components. In some embodiments, operation 404 is performed by object deployment components the same as or similar to delivery system 100, dilator 299, guide wire 201, handle 104, balloon 130, pressure gage 120, syringe 121 filled with diluted contrast solution, plunger 122 (shown in FIG. 7-13 and described herein), and/or other components.

At an operation 406, release of the object at the location before a target position is achieved is prevented. In some embodiments, operation 406 is performed by an interlock mechanism similar to and/or the same as interlock mechanism 300 (shown in FIG. 11-12 and described herein). In some embodiments, operation 406 includes preventing, with the interlock mechanism, premature release of the object before the object is balloon expanded to a predetermined pressure. In some embodiments, the interlock mechanism comprises a piston in a cylinder that is advanced through the cylinder by balloon pressure; and a spring loaded trigger operatively coupled to the piston configured to move responsive to movement by the piston to disengage a release switch to facilitate release of the object at the location in the cavity. In some embodiments, the interlock mechanism comprises an orifice and/or other components. The orifice is configured to conduct the balloon pressure to the cylinder. In some embodiments, the orifice has a diameter that is smaller than a diameter of the cylinder and a length that is shorter than a length of the cylinder. In some embodiments, the spring loaded trigger includes a body, a foot portion, and a leg portion extending between the body and the foot portion. The foot portion is operatively coupled to the piston. In some embodiments, the foot portion is supported by a ledge and configured to be pushed off the ledge by the piston and cause the spring loaded trigger to disengage the release switch.

At an operation 408, the object is secured while the object is in the cavity. In some embodiments, operation 408 is caused by a retention mechanism similar to and/or the same as the retention mechanism formed by retention tube 150 and retention fingers 151 (shown in FIGS. 10, 14, and 15-18, and described herein). In some embodiments, the retention mechanism is activated by the interlock mechanism to release the object at the location in the cavity. In some embodiments, the retention mechanism comprises an outer tube with distal fingers that protrude distally through an opening in a distal end of the object; and an inner rod or tube within the outer tube that prevents the distal fingers on the outer tube from collapsing. In some embodiments, responsive to the inner rod being withdrawn proximally with respect to the outer tube, the distal fingers of the outer tube collapse to facilitate withdrawal of the distal fingers through the opening in the (e.g., distal) end of the object, and withdrawal of the inner rod and the outer tube from the object, thereby releasing the object at the location within the cavity.

At an operation 410, the object is grasped and extracted from the location in the cavity. In some embodiments, operation 410 occurs after the object has been deployed at the location in the body. In some embodiments, operation 410 is caused by a grasping and extraction device similar to and/or the same as extraction device catheter 2, extraction device 53, and/or a sliding handle 20 and thumb grip 21 (shown in FIG. 1-6 and described herein). In some embodiments, the extraction device catheter is configured such that grasping and extraction components are located at a distal end of the extraction device catheter and actuator controls (e.g., sliding handle 20 and/or thumb grip 21) for the grasping and extraction components are located at a proximal end of the extraction device catheter. In some embodiments, the extraction device catheter is configured such that the actuator controls comprise the sliding handle and thumb grip located at the proximal end of the extraction device catheter. In some embodiments, the operation 410 comprises compressing the sliding handle and thumb grip relative to each other to cause the grasping and extraction components to grasp the object, and extending the sliding handle and thumb grip relative to each other to cause the grasping and extraction components to release the object.

In some embodiments (e.g., before the object is fully deployed at the location in the cavity), operation 410 is caused by retaining grip of the device using a combination of retention tube 150 with retention fingers 151 and an inner lock tube 155, such grip being strong enough to facilitate retrieval via eversion as described previously.

In some embodiments, the grasping and extraction components comprise jaws configured to close around the (e.g., distal) end of a vena cava filter responsive to the sliding handle and thumb grip being compressed relative to each other. In some embodiments, the object is a vena cava filter, and operation 410 includes advancing the extraction device catheter through the guiding catheter to the location of the object and grasping and securing the object responsive to the sliding handle and thumb grip being compressed relative to each other; and enabling a user to pull proximally on the end of the vena cava filter causing the vena cava filter to evert, and with continued pulling advance the vena cava filter into the guiding catheter for removal from the cavity.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to deliver a vascular filter to, and retrieve the vascular filter from, a location in a cavity, the system comprising:
   the vascular filter;
   a guiding catheter configured to provide a conduit to and from the location for the vascular filter;
   vascular filter deployment components configured to facilitate deployment of the vascular filter through the guiding catheter at the location in the cavity; and
   a retention mechanism configured to secure the vascular filter while the vascular filter is in the cavity, the retention mechanism comprising:
   (i) an outer tube with distal fingers that are configured to protrude distally through an opening in a distal end of the vascular filter; and
   (ii) an inner rod or inner tube within the outer tube that prevents the distal fingers on the outer tube from collapsing;
   wherein, responsive to the inner rod or inner tube being withdrawn proximally with respect to the outer tube, the distal fingers of the outer tube collapse to facilitate withdrawal of the distal fingers through the opening in the distal end of the vascular filter, and withdrawal of the inner rod or inner tube and the outer tube from the vascular filter, thereby releasing the vascular filter at the location within the cavity.

2. The system of claim 1, wherein the cavity is the vena cava and the vascular filter is a vena cava filter.

3. The system of claim 1, further comprising an interlock mechanism configured to prevent release of the vascular filter at the location in the cavity before a target position of the vascular filter in the cavity is achieved.

4. The system of claim 3, wherein actuation of the interlock mechanism enables the release of the vascular filter by the retention mechanism, thereby facilitating deployment of the vascular filter at the location in the cavity.

5. The system of claim 3, wherein the interlock mechanism is configured to prevent premature release of the vascular filter before the vascular filter is balloon expanded to a predetermined pressure.

6. The system of claim 3, wherein the interlock mechanism comprises:
   (i) a piston in a cylinder that is advanced through the cylinder by balloon pressure from a balloon of the vascular filter deployment components; and
   (ii) a spring loaded trigger operatively coupled to the piston configured to move responsive to movement by the piston to disengage a release switch to facilitate release of the vascular filter at the location in the cavity.

7. The system of claim 6, wherein the interlock mechanism further comprises an orifice configured to conduct the balloon pressure to the cylinder, the orifice having a diameter that is smaller than a diameter of the cylinder.

8. The system of claim 6, wherein the spring loaded trigger includes a body, a foot portion, and a leg portion extending between the body and the foot portion; the foot portion operatively coupled to the piston, the foot portion supported by a ledge and configured to be pushed off the ledge by the piston and cause the spring loaded trigger to disengage the release switch.

9. A system configured to deliver an object to, and retrieve the object from, a location in a cavity, the system comprising:
   a guiding catheter configured to provide a conduit to and from the location for the object;
   object deployment components configured to facilitate deployment of the object through the guiding catheter at the location in the cavity, the object deployment components comprising a balloon configured to expand the object at the location; and
   a retention mechanism configured to secure the object while the object is in the cavity, the retention mechanism comprising:
   (iii) an outer tube with distal fingers that are configured to protrude distally through an opening in a distal end of the object; and
   (iv) an inner rod or inner tube within the outer tube that prevents the distal fingers on the outer tube from collapsing;
   wherein, responsive to the inner rod or inner tube being withdrawn proximally with respect to the outer tube, the distal fingers of the outer tube collapse to facilitate withdrawal of the distal fingers through the opening in the distal end of the object, and withdrawal of the inner rod or inner tube and the outer tube from the object, thereby releasing the object at the location within the cavity.

10. The system of claim 9, further comprising an interlock mechanism configured to prevent release of the object at the location in the cavity before a target position of the object in the cavity is achieved.

11. The system of claim 10, wherein actuation of the interlock mechanism enables the release of the object by the retention mechanism, thereby facilitating deployment of the object at the location in the cavity.

12. The system of claim 10, wherein the interlock mechanism is configured to prevent premature release of the object before the object is balloon expanded to a predetermined pressure.

13. The system of claim 10, wherein the interlock mechanism comprises:
   (i) a piston in a cylinder that is advanced through the cylinder by balloon pressure; and
   (ii) a spring loaded trigger operatively coupled to the piston configured to move responsive to movement by the piston to disengage a release switch to facilitate release of the object at the location in the cavity.

14. The system of claim 13, wherein the interlock mechanism further comprises an orifice configured to conduct the balloon pressure to the cylinder, the orifice having a diameter that is smaller than a diameter of the cylinder.

15. The system of claim 14, wherein the spring loaded trigger includes a body, a foot portion, and a leg portion extending between the body and the foot portion; the foot portion operatively coupled to the piston, the foot portion supported by a ledge and configured to be pushed off the ledge by the piston and cause the spring loaded trigger to disengage the release switch.

16. The system of claim 9, wherein the cavity is the vena cava and the object is a vena cava filter.

17. The system of claim 9, wherein the object deployment components are configured such that the object is compressed and mounted over the balloon.

18. A system configured to deliver an object to, and retrieve the object from, a location in a cavity, the system comprising:
 the object;
 a guiding catheter configured to provide a conduit to and from the location for the object;
 object deployment components configured to facilitate deployment of the object through the guiding catheter at the location in the cavity; and
 a retention mechanism configured to secure the object while the object is in the cavity, the retention mechanism comprising:
 (v) an outer tube with distal fingers that are configured to protrude distally through an opening in a distal end of the object; and
 (vi) an inner rod or inner tube within the outer tube that prevents the distal fingers on the outer tube from collapsing;
 wherein, responsive to the inner rod or inner tube being withdrawn proximally with respect to the outer tube, the distal fingers of the outer tube collapse to facilitate withdrawal of the distal fingers through the opening in the distal end of the object, and withdrawal of the inner rod or inner tube and the outer tube from the object, thereby releasing the object at the location within the cavity; and
 wherein, before or after deployment, but prior to release of the object at the location in the cavity, the retention mechanism is configured to enable a user to pull proximally on the distal end of the object, the proximal pulling on the distal end of the object configured to cause the object to evert, and with continued pulling advance the object into the guiding catheter for removal from the cavity.

19. The system of claim 18, wherein the object deployment components comprise a balloon configured to expand the object at the location.

20. The system of claim 19, further comprising an interlock mechanism configured to prevent release of the object at the location in the cavity before a target position of the object in the cavity is achieved.

21. The system of claim 20, wherein actuation of the interlock mechanism enables the release of the object by the retention mechanism, thereby facilitating deployment of the object at the location in the cavity.

22. The system of claim 20, wherein the interlock mechanism is configured to prevent premature release of the object before the object is balloon expanded to a predetermined pressure.

23. The system of claim 22, wherein the interlock mechanism comprises:
 (i) a piston in a cylinder that is advanced through the cylinder by balloon pressure; and
 (ii) a spring loaded trigger operatively coupled to the piston configured to move responsive to movement by the piston to disengage a release switch to facilitate release of the object at the location in the cavity.

24. The system of claim 23, wherein the interlock mechanism further comprises an orifice configured to conduct the balloon pressure to the cylinder, the orifice having a diameter that is smaller than a diameter of the cylinder.

25. The system of claim 23, wherein the spring loaded trigger includes a body, a foot portion, and a leg portion extending between the body and the foot portion; the foot portion operatively coupled to the piston, the foot portion supported by a ledge and configured to be pushed off the ledge by the piston and cause the spring loaded trigger to disengage the release switch.

26. The system of claim 18, wherein the cavity is the vena cava and the object is a vena cava filter.

\* \* \* \* \*